(12) United States Patent
Wieczorek

(10) Patent No.: US 7,683,333 B2
(45) Date of Patent: Mar. 23, 2010

(54) DETECTOR FOR NUCLEAR MEDICINE

(75) Inventor: Herfried K. Wieczorek, Aachen (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 442 days.

(21) Appl. No.: 11/577,093

(22) PCT Filed: Sep. 30, 2005

(86) PCT No.: PCT/IB2005/053231

§ 371 (c)(1),
(2), (4) Date: Apr. 12, 2007

(87) PCT Pub. No.: WO2006/040707

PCT Pub. Date: Apr. 20, 2006

(65) Prior Publication Data

US 2009/0022279 A1    Jan. 22, 2009

Related U.S. Application Data

(60) Provisional application No. 60/619,080, filed on Oct. 15, 2004, provisional application No. 60/636,745, filed on Dec. 16, 2004.

(51) Int. Cl.
*G21K 1/02* (2006.01)

(52) U.S. Cl. .................................................. 250/363.1

(58) Field of Classification Search ............... 250/363.1
See application file for complete search history.

(56) References Cited

U.S. PATENT DOCUMENTS

| | | | |
|---|---|---|---|
| 4,066,901 A | 1/1978 | Seppi et al. | |
| 4,277,684 A | 7/1981 | Carson | |
| 5,198,680 A | 3/1993 | Kurakake | |
| 5,311,427 A | 5/1994 | Ichihara | |
| 6,324,258 B1 | 11/2001 | Beckman | |
| 6,483,891 B1* | 11/2002 | Lazarev et al. | 378/37 |
| 6,693,291 B2* | 2/2004 | Nelson et al. | 250/505.1 |
| 6,762,413 B2* | 7/2004 | Zeng | 250/363.1 |
| 6,967,331 B2 | 11/2005 | Van Dulmen et al. | |
| 2004/0044282 A1* | 3/2004 | Mixon et al. | 600/427 |

FOREIGN PATENT DOCUMENTS

EP    1120086 A1    8/2001

OTHER PUBLICATIONS

Accorsi, R., et al.; Analytic Determination of the Resolution-Equivalent Effective Diameter of a Pinhole Collimator; 2004; IEEE Trans. on Medical Imaging; 23(6)750-763.

(Continued)

*Primary Examiner*—David P Porta
*Assistant Examiner*—Mindy Vu

(57) ABSTRACT

A radiation imaging device suitable for SPECT or other nuclear imaging includes a detector (22) which receives radiation. A fan beam-slit collimator (20) is positioned adjacent a radiation receiving face (32) of the detector, intermediate the detector and a radiation source (12, 18). The collimator includes a plurality of slats (30) having a common focus. A body (44) adjacent the slats defines one or more elongate slits (46). The slit is arranged such that radiation passes through the slit and between the slats to the detector face. The body is at least substantially impermeable to the radiation. The fan beam-slit collimator (20) enables higher resolution or efficiency to be achieved from the detector.

20 Claims, 5 Drawing Sheets

OTHER PUBLICATIONS

Brice, J. SPECT rides first wave of clinical MI applications; 2003; Diagnostic Imaging; http://www.dimag.com/molecularimagingoutlook/2003sep/.

Brice, J. Nanoparticles pack heavyweight punch; 2004; Diagnostic Imaging; http://www.dimag.com/molecularimagingoutlook/2004mar/03.jhtml.

Gagnon, D., et al.; Design Considerations for a New Solid-State Gamma-Camera: Solstice; 2001; IEEE Nuclear Science Symposium Conference Record; pp. 1156-1160.

Gindi, G. R., et al.; Imaging with rotating slit apertures and rotating collimators; 1982; Med. Phys.; 9(3)324-339.

Goedicke, A., et al.; Image Quality Assessment of Pixellated Systems; Oct. 2004.

Lodge, M. A., et al.; The experimental evaluation of a prototype rotating slit collimator for planar gamma camera imaging; 1995; Phys. Med. Biol.; 40:427-448.

Petrillo, M., et al.; Imaging Performance of Tiled Solid-State Detectors; Oct. 2004.

Reckess, G. Z.; Nano-targeting cancer and heart disease; 2003; http://news-info.wusl.edu/tips/page/normal/203.html.

Rogers, W. L., et al.; Sprint II: A Second Generation Single Photon Ring Tomograph; 1988; IEEE Trans. on Medical Imaging; 7(4)291-297.

Webb, S., et al.; Monte Carlo modelling of the performance of a rotating slit-collimator for improved planar gamma-camera imaging; 1992; Phys. Med. Biol.; 37(5)1095-1108.

\* cited by examiner

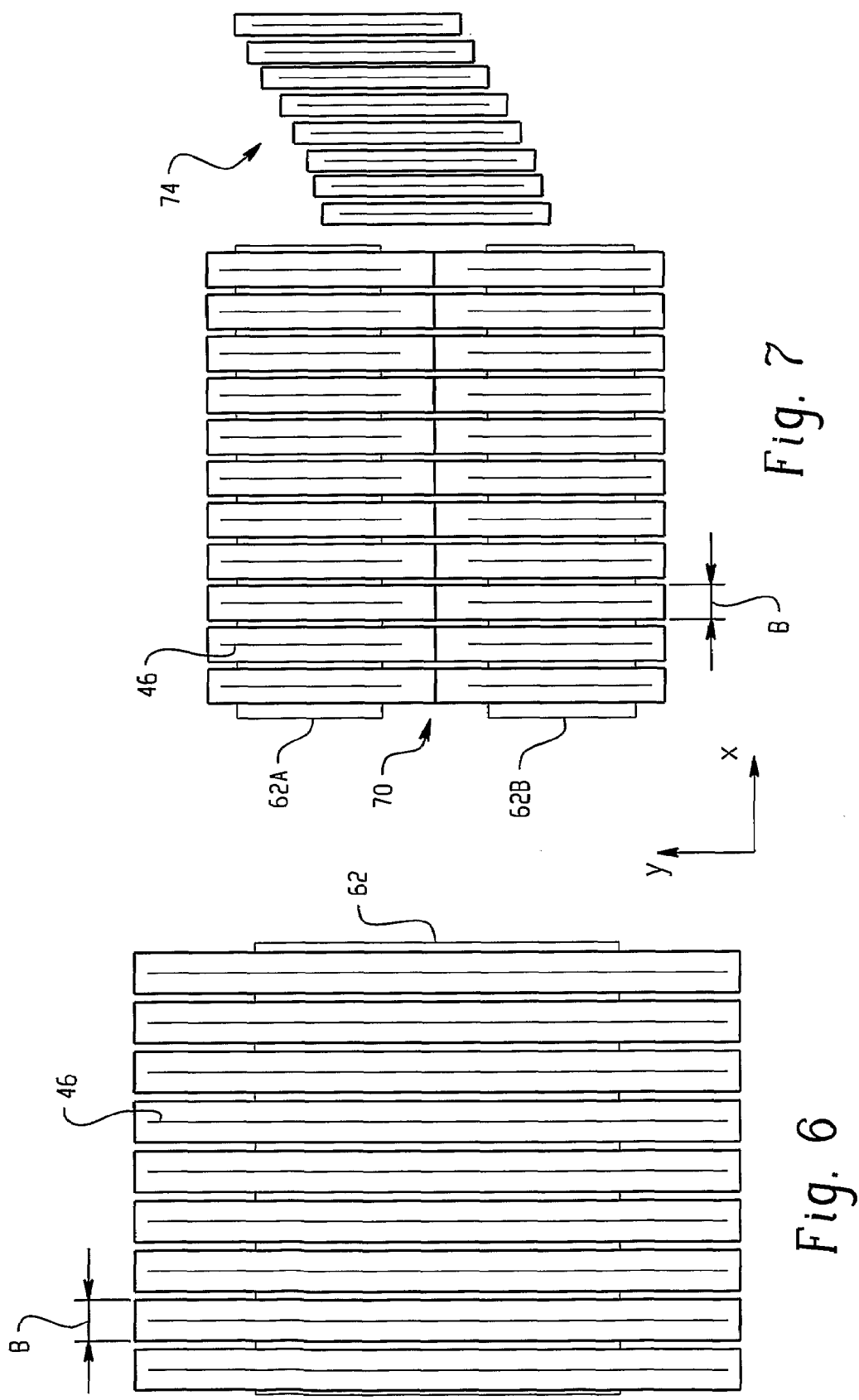

DETECTOR FOR NUCLEAR MEDICINE

CROSS REFERENCE TO RELATED APPLICATIONS

This application claims the benefit of U.S. provisional application Ser. No. 60/619,080 filed Oct. 15, 2004 and U.S. provisional application Ser. No. 60/636,745, filed Dec. 16, 2004, both of which are incorporated herein by reference.

The present application relates to the production of images with a nuclear camera. It finds particular application in conjunction with a fan beam collimator having a slit, and will be described with particular reference thereto. However, it is to be appreciated that the present exemplary embodiment is also amenable to other like applications.

Nuclear imaging techniques generally obtain images in one of two different ways. Emission images are generated by introducing a radioactive isotope to the subject and collecting radiation coming from within the subject with a detector sensitive to such radiation (camera). Such emission images include Single Photon Emission Computed Tomography (SPECT) images and are often used to provide functional information regarding the subject, such as a tumor within a patient. When several emission projection images are made, in mutually different directions, it is possible to compute (reconstruct) from the obtained data the concentration distribution of the radiation-generating matter in the object in the form of a volumetric emission tomography image.

Transmission images are generated by positioning the subject intermediate a radiation source, such as a source of gamma radiation, and the detector so that the radiation that passes through the subject is detected with the camera. Transmission images provide information about the distribution of radiation-attenuating or radiation-absorbing matter in the subject.

Transmission images and emission images are often performed simultaneously, for example, for correction of the emission image for attenuation of the radiation in the object. For example, a SPECT imaging device is sometimes used to generate both emission and transmission images.

Photons generated inside and transmitted through the subject are detected by the detector, such as an NaI crystal and an array of photomultipliers. To define a trajectory of each received emission event and to discriminate between direct radiation and scattered radiation, a collimator is placed before the camera. In transmission imaging, a predetermined spatial geometry of the radiation source also determines the trajectory of the transmission radiation events. The collimator, which includes a grid or honeycomb-like array of radiation absorbent material, is located between the detector and the subject being examined to limit the angle of acceptance of radiation which impinges on the detector. Resolution and efficiency are defined by the shape of the collimator and the height and thickness of septa defining grid, with thicker septa generally being used for higher energy ranges.

One problem in SPECT imaging is the limited detector efficiency for a given spatial resolution. Current Anger cameras differ in their relative optimizations. Static detectors (i.e., those which maintain the same general orientation towards the radiation source) for planar or SPECT imaging include parallel hole, fan beam, cone beam, and pinhole collimation. The parallel hole detector includes a collimator with parallel slats in a first direction which intersect parallel slats in a second direction. The collimator is used in combination with a planar source for transmission measurements. The efficiency of such a collimator is relatively low because the planar radiation source radiates radiation in all directions within a particular solid angle, but only a very limited portion is utilized in making the transmission image, namely, only the portion that is directed in the direction of the passages of the collimator. As a consequence, a relatively strong source is used for making a transmission image with a predetermined brightness.

Improvements in efficiency over the parallel hole detector may be achieved by focused collimators in which the slats are oriented towards a focus which is at the same side of the collimator as the object to be measured. A fan beam collimator includes slats which are focused in one direction and which are parallel in the other direction. The fan beam collimator is used with a line radiation source for transmission measurements which is arranged along the focal line. A cone beam collimator includes slats which are focused in both directions and may be used with a point radiation source at the focal point for transmission measurement. The use of a line source together with a fan beam collimator or a point source with a cone beam collimator provides an advantage over the combination of a planar source and a parallel collimator in that the radiation produced is better utilized, and hence the amount of radioactive matter of the radiation source can be less. Further, the emission and transmission recordings are improved because converging collimators, due to the magnifying effect, count more photons than do parallel collimators. However, the improvements which can be achieved by such focused collimators are limited, especially for higher energy photons which require thick septa and cause partial shadowing of the pixels.

As an alternative to static detector systems, dynamic detector concepts have been proposed, among them rotating slat or slit detectors, coded aperture imaging, and overlapping detector regions. These concepts tend to suffer from noise accumulation due to the necessary extra reconstruction step.

In accordance with one aspect of the present exemplary embodiment, a radiation imaging device is provided. The imaging device includes a detector. A collimator is positioned adjacent a radiation receiving face of the detector. The collimator includes a plurality of slats having a common focus. A body, adjacent the slats, defines an elongate slit. The slit is arranged such that radiation passes through the slit and between the slats to the detector. The body is at least substantially impermeable to the radiation.

In accordance with another aspect, an imaging method is provided. The method includes directing radiation from a source towards a detector and interposing a slit and a plurality of spaced slats having a common focus between the radiation source and the detector, whereby radiation passes through the slit and between the slats onto the detector.

In accordance with another aspect, a detection system is provided. The detection system includes a detector which defines a plurality of pixels. A plurality of spaced slats have a common focus and define passages therebetween, each of the passages extending adjacent a row of the pixels. A plate covers the slats and defines a slit. The slit has a width and a length perpendicular to the width. The length is greater than the width and greater than a spacing between the slats, whereby radiation entering the slit travels through the passages to the detector pixels.

An advantage of at least one embodiment arises from the ability to achieve higher efficiencies than for other static detector concepts.

Still further advantages and benefits of the present invention will become apparent to those of ordinary skill in the art upon reading and understanding the following detailed description of the preferred embodiments The invention may take form in various components and arrangements of components, and in various steps and arrangements of steps. The drawings are only for purposes of illustrating the preferred embodiments and are not to be construed as limiting the invention.

FIG. 6 is a top plan view of a second embodiment of a detection system for the nuclear imaging system of FIG. 1; and FIG. 7 is a top plan view of a third embodiment of a detection system for the nuclear imaging system of FIG. 1.

Figure 1:
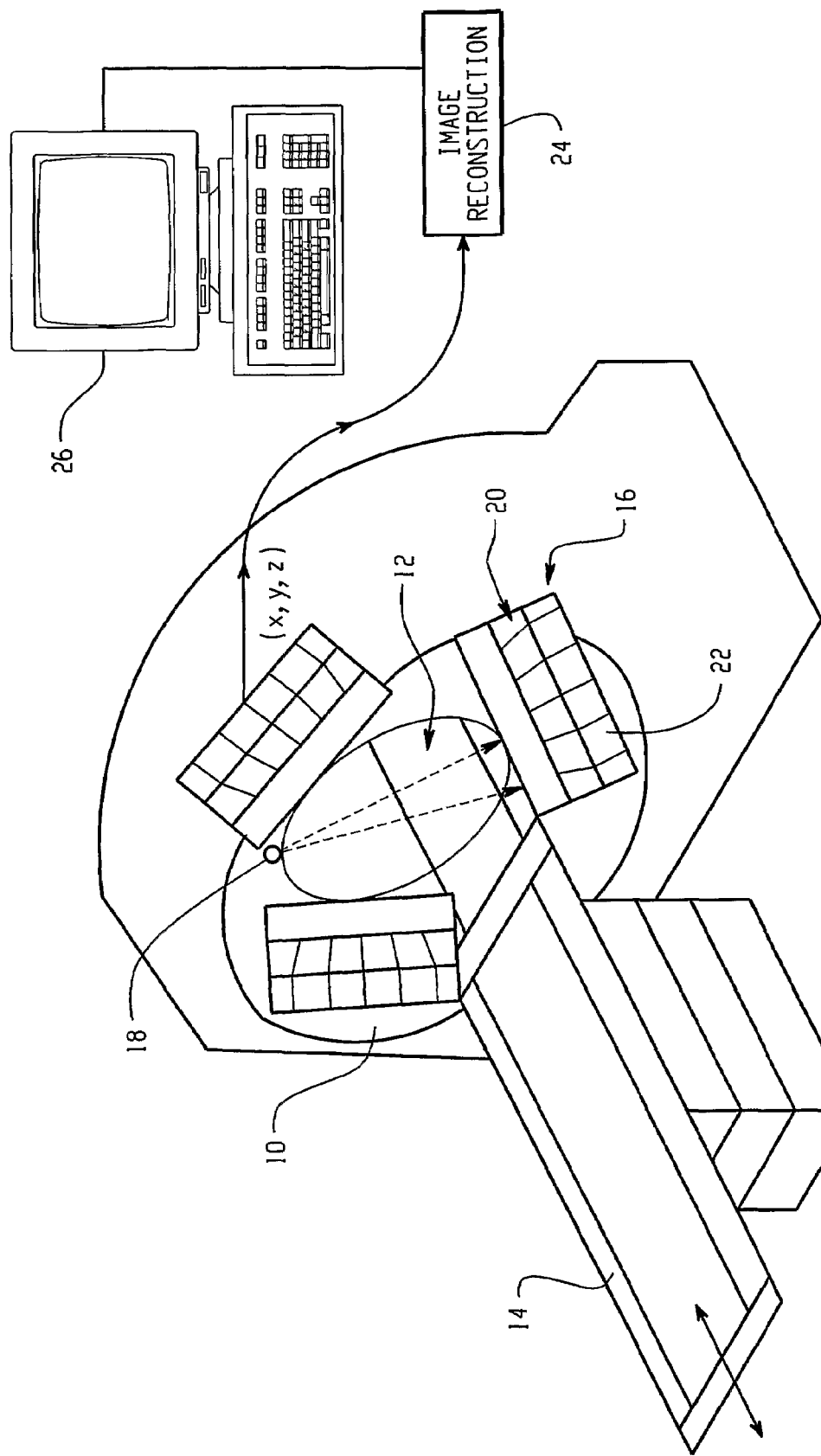
FIG. 1 is a perspective view of a nuclear imaging system according to the present embodiment.

With reference to FIG. 1, a perspective view of an imaging system for generation of transmission images or combined emission/transmission images is shown. The imaging system includes an imaging region 10 in which a subject, such as a patient 12 lies or is transported therethrough on a moveable support 14. One or more radiation detection systems or heads 16 are positioned adjacent to the patient to monitor and record transmitted and/or emitted radiation events. A source of transmission radiation 18, such as a gamma radiation source, is positioned such that radiation emitted by the source enters the subject and received in the form of photons by an opposing detection system 16. Alternatively or additionally, a radiopharmaceutical introduced to the subject 12 serves as a source of radiation for SPECT imaging. Typically, the emission and transmission radiation have different energies to facilitate differentiating them. The detection system includes a collimator 20 and a detector 22. The collimator is positioned intermediate the subject 12 and the detector 22 to limit the angle of acceptance of radiation which impinges on the detector. The detector 22 is linked to a processing system 24, which may be embodied in an operator work station, computer network, or other suitable hardware/software. The processing system 24 reconstructs an image of the subject, based on signals from the detector, which is displayed by a display 26, such as a screen or printout.

The detector 22 includes a sensor, which detects radiation (typically photons) generated as a result of the interaction of the radiation with the subject. One suitable sensor includes a scintillator, such as a single crystal, such as a sodium iodide crystal, or a matrix of smaller crystals. The crystal is positioned adjacent a matrix of photomultiplier tubes ("PMTs"). Each radiation event impinging on the scintillator generates a corresponding flash of light (scintillation) that is seen by the PMTs. Based on the outputs from the PMTs, radiation events are mapped, which include the energy and position of radiation rays impinging the scintillator. Other detectors include a matrix of scintillation crystals, i.e. a pixelated detector, which are mated with photodiodes or avalanche detectors in place of photomultiplier tubes. Alternatively, a cadmium zinc telluride (CZT) or other direct conversion detector is used which converts radiation photons directly to electrons (current) without a scintillator.

The image quality of the SPECT images is typically determined by a count sensitivity of the detector and the geometry of the collimator.

Figure 2:
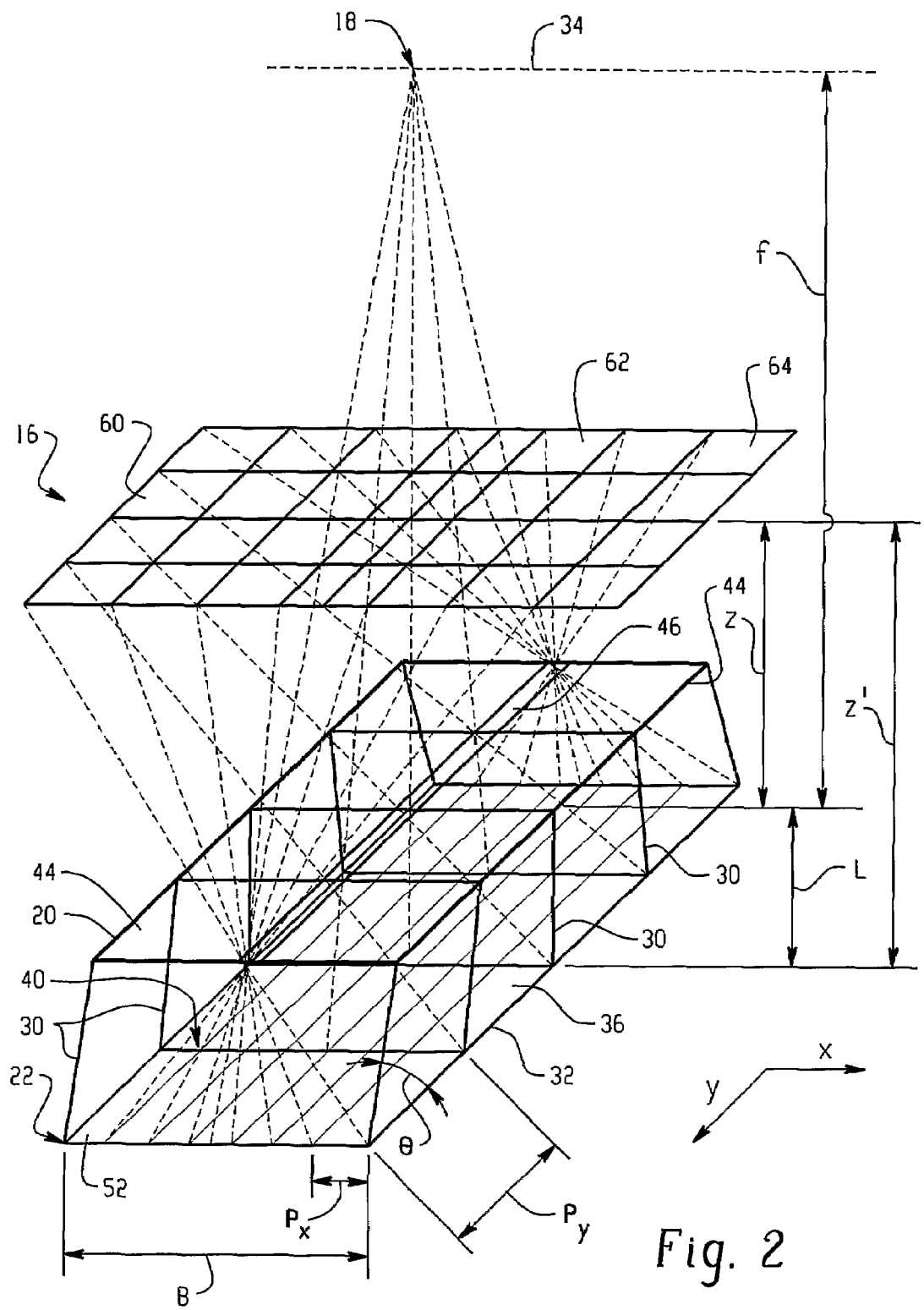
FIG. 2 is a perspective view of a first embodiment of a detection system for the nuclear imaging system of FIG. 1.
Figure 3:
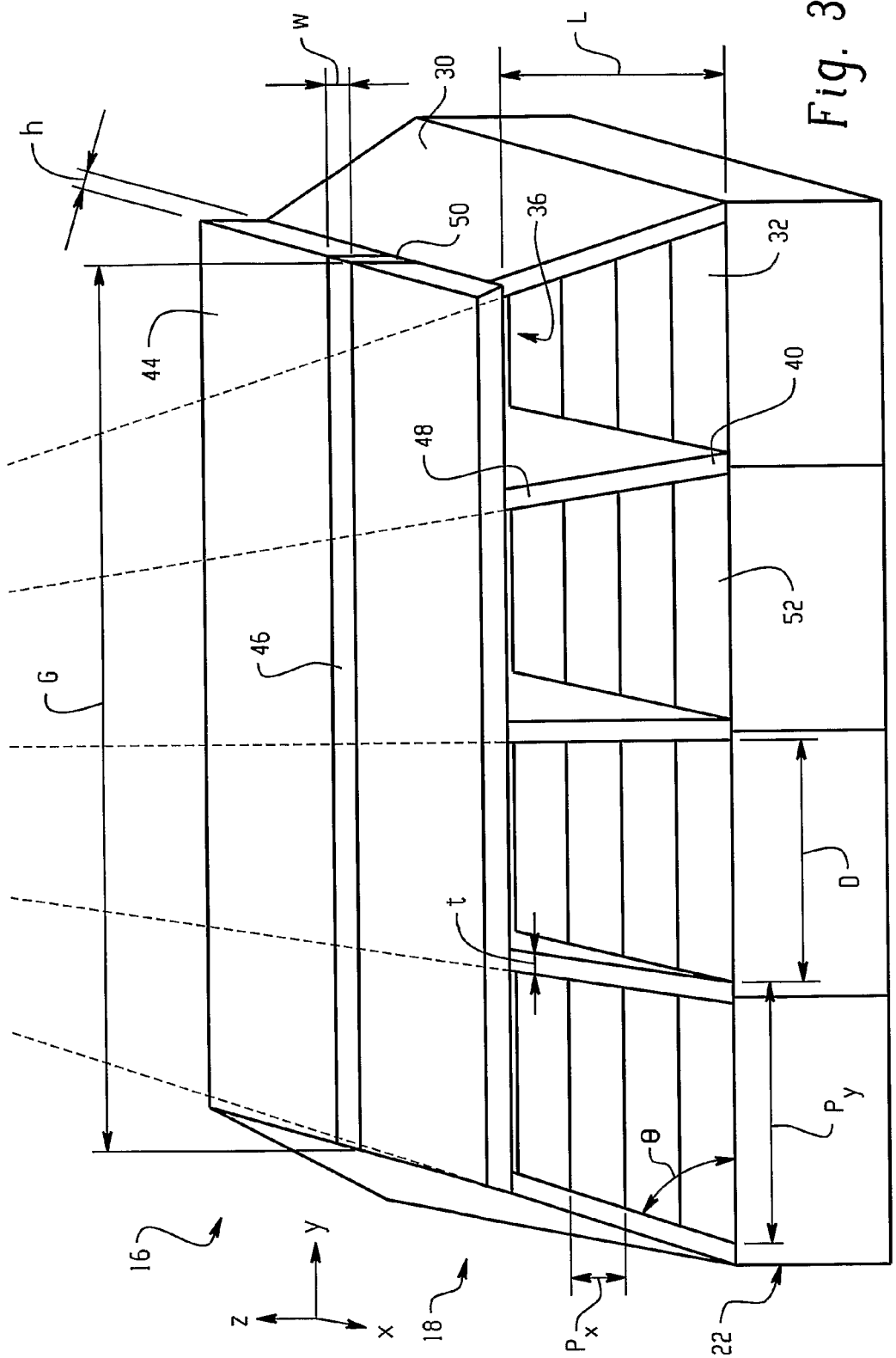
FIG. 3 is a side perspective view of the detection system of FIG. 2.

With reference now to FIGS. 2 and 3, the collimator 20 is formed of a dense radiation absorbing material, such as tungsten. The collimator 20 can be regarded as a transmission means with a direction-selective transmission characteristic, which ensures that a detection segment of the detection surface of the detector can only be irradiated by radiation with a predetermined limited range of directions. The presently illustrated collimator can be described as a fan beam-slit collimator. The fan beam portion of the collimator is provided by a plurality of closely spaced slats or septa 30 (five are illustrated but the number is typically much larger). The slats 30 are planar. In the illustrated embodiment, a generally planar radiation receiving face or detection surface 32 of the detector 22 lies in a plane defined by y and x axes and the collimator slats 30 extend away from the plane generally in a z direction. Specifically, the slats 30 extend from the planar surface 32 of the detector towards the radiation source 18 and converge towards a focal line 34. In the illustrated embodiment, the source 18 comprises a line source which is collinear with the focal line 34 of the slats for optimal efficiency, although it is also contemplated that the source may be spaced further from, or closer to the detector 22. Although there may be only a single transmission source opposite one of a plurality of heads, all heads have a common collimator. Due to the convergence, the outer slats are oriented at a shallower angle θ to the plane of the detector than the inner slats, the angle θ increasing towards the center, where the center slat is oriented at, 90° to the plane x, y. The slats 30 define a plurality of parallel passages 36 therebetween. As a result of the focused slats, a centerline of each passage intersects the line-shaped radiation source 18. The passages 36 extend the full width B of the detector plane in the x direction, i.e., there are no intersecting slats as in a conventional fan beam or cone-shaped collimator.

Ends 40 of the slats closest to the detector 22 are equally spaced, adjacent the detector in the y direction, with a pitch P. Preferably, the ends 40 of the slats are spaced to coincide with the interface between adjacent rows of elements of a pixelated detector. Due to the thickness of the slats t, the distance between adjacent slats D=P−t. The slats have a height L in the z direction and a width B in the x direction, which is greater than the height L. In one embodiment, the pitch $P_y$ is about 1-3 mm, the distance between adjacent slats D is about 0.80 to about 2.95 mm, the thickness of the slats t is about 0.05 mm to about 0.5 mm, e.g., about 0.15 mm, the height L is from about 10 mm to about 100 mm, and in one specific embodiment, L is less than about 60 mm.

The slit portion of the collimator is defined by a body generally in the form of a plate 44 which lies in a plane parallel to the plane 36 of the detector 22. The plate is formed of a radiation opaque material, such as a radiation impermeable, or substantially impermeable material. As best shown in FIG. 3, the plate defines an elongate slit 46 which extends a length G of the detector in the y direction, which is greater than the distance $P_y$ between slats. The slit has a width w in the x direction. Length G is substantially greater than the width w. In one embodiment, w is from about 0.3 mm to about 3 mm, the narrower the slit, the higher the resolution. The plate 44 has a thickness h in the z direction, which is the height of the slit 46, of from about 0.5 mm to about 5 mm, the higher thickness being more suited to higher energies. In the illustrated embodiment, the plate 44 is located at height L above the plane 32, i.e., in contact with upper ends 48 of the slats 30 although it is also contemplated that the plate may be spaced from the plane by a distance somewhat greater than L, but generally less than 2L. The focus 34 is located a distance d f from the plane 44. Side walls 50 of the slit may be aligned with the z axis, as shown, or angled to the z axis, for example in a V shape or an inverted V shape.

The illustrated detector 22 is pixellated. As shown in FIG. 2, a row of pixels 52 extends between each pair of adjacent slats 30. The pixels are configured for independently sending signals to the processing system 24. The pixels each have a pixel width or pitch $P_x$ in the x direction and a length D in the y direction. In one embodiment, $P_x$ is from about 0.5 mm to about 2.5 mm. Seven pixels 50 are illustrated in each row/passage, although a much greater number of pixels is typically employed. In one embodiment, the pixel pitch $P_x$ is greater than or equal to half the slit width w but less than the interval between slits.

Radiation from an object plane 60 spaced a height z above the plane 44 accesses the detector 22 only through the slit 46, as shown by the hatched lines in FIG. 2. The field of view (FOV) 62 is the area within the plane. The area of the projected image on the detector, which in the embodiment of FIG. 2 is defined by the area of the plane 32, is smaller in the x direction than the object plane. As can be seen from FIG. 2, each pixel 52 in the detector has an area $P_x \times D$, which is smaller in the x direction and larger in the y direction than the area of a corresponding pixel 64 in the object plane, resulting in a magnifying effect in the y direction.

It will be appreciated that the detector plane 32 is typically larger than the projected image, for example, where multiple slits and/or multiple modules are employed. Where the detection system 16 includes multiple slits 46, each slit serves a different portion, or partially overlapping portion of the detector plane 32, to increase the area of detection. In one embodiment, the slits are oriented parallel to one another, as illustrated in FIGS. 6 and 7, each slit and its associated slats comprising a module. The slats of one module may be continuations of the slats of an adjacent module. Or, more than one module may share the same slit. In one embodiment, the spacing S between adjacent slits is from about 5 to 100 mm, and in one specific embodiment, from 5 to 50 mm (FIG. 7).

In the illustrated embodiment, the detector 22 is a static detector, i.e., does not rotate but remains fixed, relative to the slats and detector plane. The entire detector system 16 may, of course, rotate around the subject, for example, by means of a rotating gantry. The fan beam-slit collimator finds particular application in planar or SPECT imaging. Planar imaging is performed without rotation of the detector about the patient. The detector is also suitable for use in a rolec-type camera in which the detector rotates about an axis that is perpendicular to the detector plane.

The fan beam-slit arrangement is beneficial for optimizing efficiency while maintaining resolution. In one embodiment, simultaneous optimization of slat length (for the fan beam) and collimator-detector distance (for the slit) in combination with parallel readout of neighboring detector areas which is possible when slit collimators are used with solid state detectors in de-magnification mode, provides a performance which exceeds that of conventional detection systems. As will be appreciated, where thick slats are used for high energy photons, the optimization is not completely possible, but efficiency values are still high.

An analytical model for spatial resolution and geometric efficiency of a collimator in combination with a pixellated detector, such as a pixellated CZT-based detector, can be derived. Descriptions for static and rotating detector concepts can be derived, for example, using National Electrical Manufacturers Association (NEMA) performance criteria for detection efficiency and measures adapted for spatial resolution of pixellated detectors, based on the sampling of the single pixel response function.

Tradeoffs among resolution, efficiency, and signal-to-noise ratio (SNR) have been investigated for different applications. The analysis shows that the concept of rotating collimators suffers from noise accumulation, except for purely hot spot imaging. The fan beam-slit collimator in a demagnification mode provides optimum efficiency and image quality using pixellated solid-state detectors for SPECT cameras.

Without being bound to a particular theory, the following considerations demonstrate a theoretical basis for the improved efficiency of the fan beam-slit collimator. Classical theory describes collimator performance by a radioactive point source whose radiation is projected through the collimator passages and absorbed in the detector. Due to the shadowing effect of the collimator septa, the illuminated pixel area decreases linearly with the distance from the point on the detector directly underneath the point source. A disadvantage of this model results from an understanding that the point source response function is not space invariant.

For pixellated detectors, an alternative approach, based on the response function of a single collimator passage, is proposed, which is far better suited. It enables the derivation of exact equations for geometric efficiency and spatial resolution for a variety of collimator concepts. Based on the equations developed, it is possible to evaluate the image quality of static and rotating collimators and develop concepts for their optimization.

Collimator geometry can be defined by hole diameter D, septa thickness t, pitch P=D+t, septa length L, object plane-collimator distance z, and object plane-detector distance z'=z+L.

Figure 4:
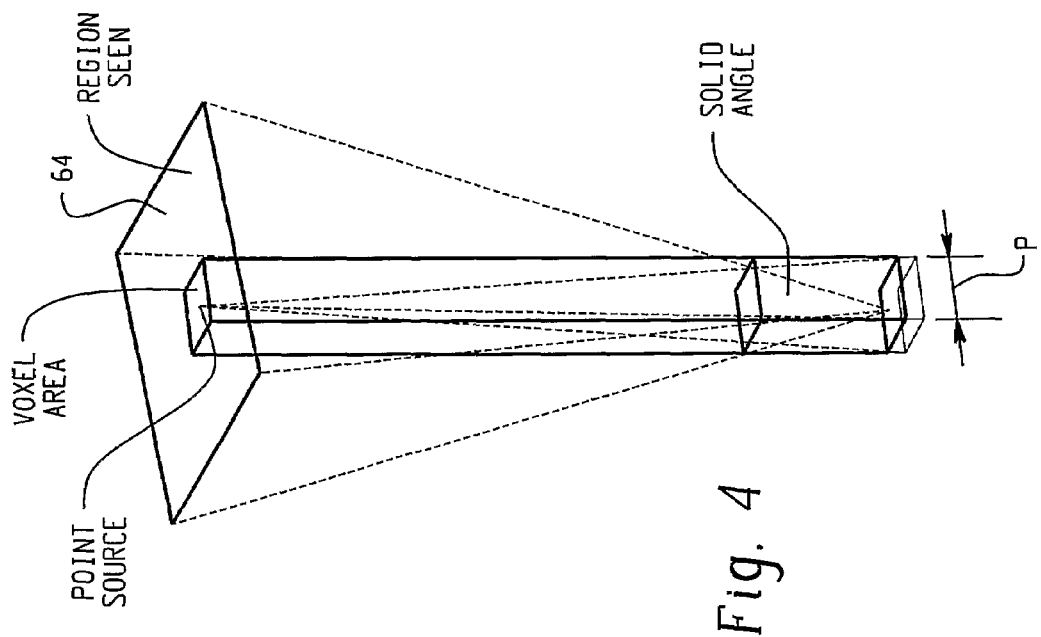
FIG. 4 is a schematic perspective view of a detector pixel demonstrating the efficiency of a collimator.

Geometric efficiency E is calculated as part of the radiation from a point source that irradiates the open detector area of one pixel (normalized solid angle), multiplied by the average area in the object plane that is seen by any point on the detector pixel (region seen) and normalized by the area of the object plane equivalent to one pixel (voxel area) as shown schematically in FIG. 4.

Figure 5:
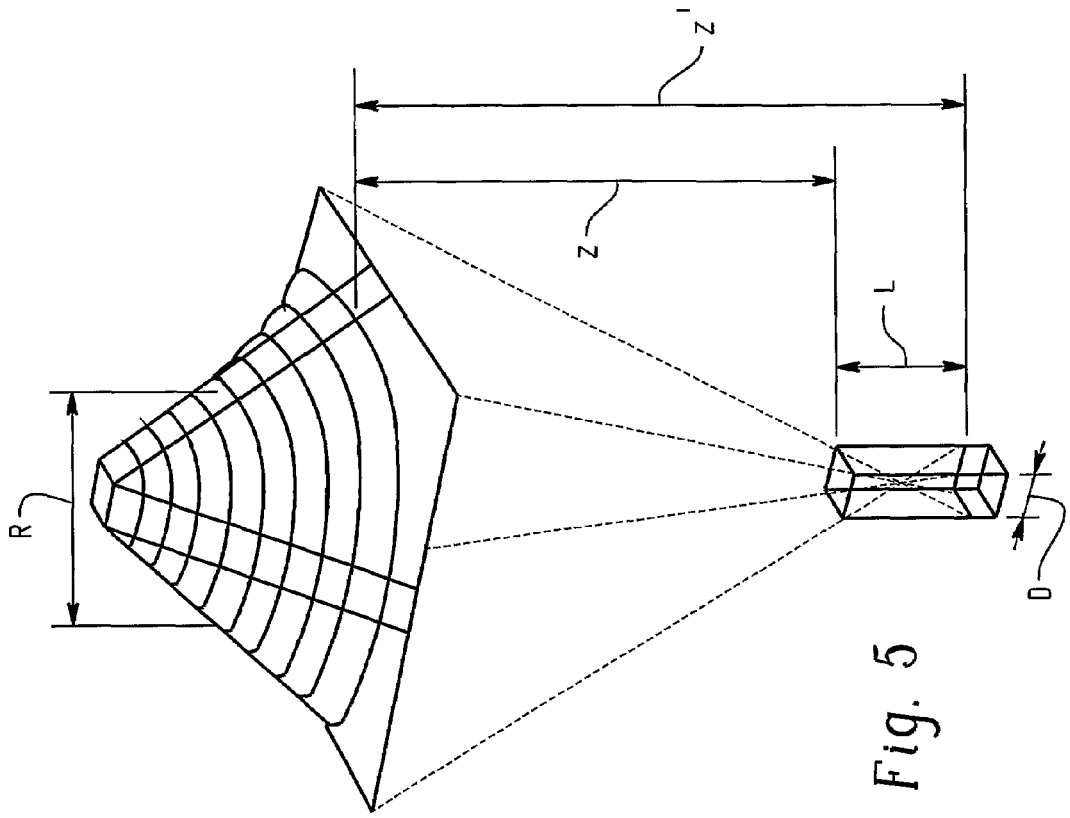
FIG. 5 is a is a schematic perspective view of a detector pixel demonstrating the spatial resolution of a collimator.

Resolution R (FIG. 5) is calculated as the full-width at half-maximum (FWHM) of the single pixel detector response for a point source in the object plane, integrated in one dimension. This definition is equivalent to the standard measurement method used in solid-state x-ray imaging where a line phantom is slightly tilted with respect to one of the detector axes.

Focused collimators provide higher efficiency at the expense of a smaller field-of-view (FOV) or, equivalently, larger detector area. The linear magnification factor m of a collimator with focal length f is:

$$m = f'/(f-z), \text{ where } f' = f + L.$$

Presuming z<f, the solid angle is reduced by a factor $\cos^3 \beta$ for all pixels outside the center part of the detector, explained by the oblique angle of incidence $\beta$ and the larger object-detector distance. The region seen is reduced by a factor f/f' or $(f/f')^2$, and the voxel area is given by the pixel area divided by m for a fan beam (for a cone beam the voxel area is given by the pixel area divided by $p^2/m^2$).

For a focussed collimator with a slit (the fan beam-slit collimator) the linear magnification factor m is defined by the slit geometry in the x direction and the pixel pitch $p_y$ defined by the slats in the y direction. Specifically:

Hole size: slit: $D_x = RL/z'$, slat distance: $D_y = RLf'/z'f$, $D_y > D_x$.

Pixel: in x:

$$p_x = \frac{D_x z'}{2z},$$

in y: $p_y = D_y + t$, $p_y > p_x$.

Magnification in x: $m_x = L/z$ (strong de-magnification)

Magnification in y:

$$m_y = \frac{f'}{f' - z'} = \frac{f'}{f - z}, \quad f' = f + L. \quad \text{(magnification)}$$

Efficiency:

$$E = a_{cone} \frac{D_x D_y^2}{4\pi Lz} \frac{f_y}{f_y - z} \cdot \frac{1}{p_y}. \quad f_y = f\text{(focal length)}$$

$a_{cone}$ is a correction factor for the limited efficiency due to the opening angle.

Resolution:

$$R_x = D_x \frac{z'}{L}, \quad R_y = D_y \frac{z'}{L} \frac{f_y}{f_y'}$$

Higher efficiency can thus be obtained by a combination of fan beam and slit, using a larger detector size in the y direction.

As an example, the performance of different detectors for general purpose imaging can be determined, as shown in Table 1. Table 1 shows performance parameters of pixellated detector concepts, six of conventional type and two with fan beam-slit collimators of the type disclosed herein.

As discussed above, collimator geometry is defined by pixel size D, septa length or collimator-detector distance L. Performance is given in terms of spatial resolution R, efficiency E, space-bandwidth product, SBP, which is essentially the number of detector pixels when the Nyquist criterion is fulfilled. Another method of expressing efficiency is as the efficiency-space-bandwidth product, ESBP, a measure of the amount of information received by different collimators. All detector values are calculated for 0.152 mm septa thickness (VXGP) and 5 mm resolution at 100 mm source-collimator distance.

Two configurations of a fan beam-slit collimator are considered. Both employ more than one module, i.e., a plurality of slits. In both cases, five slits were used. The focus of the slats, f (and the location of the source) was 10-20 cm. In configuration 1, shown in FIG. 6 (55 cm×73.3 cm in Table 1), the field of view 62 (FOV) is 55 cm in the x direction and 40 cm in the y direction. The slits 46 are oriented in the y direction, the slats (not shown) are oriented in the x direction. Several modules sharing a long slit overlap the 40 cm FOV 62 in the y direction. A large number of modules cover the 55 cm FOV in the x direction. Due to the large opening angle of the fan beams in the y direction, the average efficiency is reduced (the correction factor $a_{cone}$ given above is much smaller than 1).

In the second configuration (FIG. 7) two detector module arrangements (called 'rings' if they form part of a ring around the object) with 55 cm in the x direction and a much smaller size in y are shown. A third detector module arrangement is shown under a different SPECT angle. Modules are smaller in the y direction, therefore the opening angle is smaller and the efficiency is higher (the correction factor $a_{cone}$ given above is nearly equal to 1). Each of the module 'rings' sees only the corresponding region 62A, 62B. The missing region 70 in between the rectangles 62A, 62B is imaged by a shift of the detector rings in y or by additional detectors 74 under different SPECT angles, as shown in FIG. 7. The efficiency per detector area is much higher than in configuration 1. Optimizing for maximum efficiency of static detector concepts, it has been found that a combination of fan beam and slit, employing a detector with focused septa in one dimension and a pinhole detector in the other dimension, gives a higher efficiency than other known static detector arrangements.

In Table 1, the first value of D for the Fan Beam Slit configurations 1 and 2 corresponds to the distance between the slats in the y direction and the second value of D corresponds to the slit width w.

As shown in Table 1, the ESBP of a fan-beam slit collimator is more than 50% higher than the value for a parallel hole collimator when the concept is applied on a large camera (Configuration 1), and it is more than 250% of the parallel hole collimator value when the concept is applied on small modules or rings (Configuration 2), which is a two times higher efficiency than for other detector concepts, such as multi-pinhole. This high value is achieved by a five-fold number of readout channels and an 83% larger detector area compared to a parallel hole detector.

High efficiency can thus be achieved with only moderate increase in detector area and number of readout channels (compared to a multi-pinhole detector concept).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

TABLE 1

| | Detector area (cm$^2$) | D (mm) | L (mm) | R (mm) | E* 1E6 | SBP | ESBP |
|---|---|---|---|---|---|---|---|
| Parallel hole (optimized) | 55 × 40 | 0.733 | 17.18 | 5 | 59.6 | 35200 | 2.10 |
| Fan beam, f = 500 mm (fan axis perpendicular to z-axis) | 55 × 71.2 | 0.812 | 18.56 | 5 | 69.9 | 35200 | 2.46 |
| Fan beam, f = 500 mm (fan axis parallel to z axis) | 75.7 × 40 | 0.812 | 18.56 | 5 | 64.4 | 35200 | 2.27 |
| Cone beam, f = 500 mm | 88 × 64 | 1.833 | 50 | 5 | 63.7 | 35200 | 2.24 |
| Pinhole, 25 mm (16 × readout) | 55 × 40 | 1.0 | 25 | 5 | 60 | 35200 | 2.11 |
| Pinhole, 12.5 mm (64 × readout) | 55 × 40 | 0.56 | 12.5 | 5 | 72 | 35200 | 2.53 |
| Configuration 1 Fan beam, 250 mm, fan axis perpendicular to z-axis, slit parallel to z axis (5 × readout) | 55 × 73.3 | 1.0/ 0.9 | 20 | 5 | 92 | 35200 | 3.24 |
| Configuration 2 Fan beam-slit (small ring as above, 5 × readout) | 55 × small rings | 1.0/ 0.9 | 20 | 5 | 153 | 35200 | 5.39 |

Having thus described the preferred embodiments, the invention is now claimed to be:

1. A nuclear imaging device including at least one radiation imaging device comprising:
   a two-dimensional array of radiation detectors which detect emission radiation from radioisotope decay from an object;
   a slit disposed to project the emission radiation on the two-dimensional array of radiation detectors;
   a plurality of slats disposed orthogonal to the slit between the slit and the two-dimensional detector array, the slats converging from the detector array towards a focal line disposed further from the detector array than the object.

2. The nuclear imaging device of claim 1, further including:
   a line radiation source.

3. The nuclear imaging device of claim 1, wherein the slit is defined in a plate and the slats extend from a face of the two-dimensional detector array to the plate.

4. The nuclear imaging device of claim 1, wherein an object plane is defined through the object parallel to the two-dimensional detector array and the projection of the object plane on the two-dimensional detector array is smaller in at least one dimension than the object plane.

5. The nuclear imaging device of claim 1, wherein the slit has a width and a length, the width of the slit being less than the length of the slit, and the two-dimensional detector array includes more than two adjacent detector pixels each having a width, parallel with the width of the slit, which is equal or greater than half the width of the slit.

6. The nuclear imaging device of claim 1, wherein the slats have a pitch, equal to a length of detector pixels in a direction parallel to the slit, the pitch is from about 1 to about 3 mm and the slats have a thickness of from about 0.05 mm to about 0.5 mm.

7. The nuclear imaging device of claim 1, wherein the nuclear imaging device is a Single Photon Emission Computed Tomography (SPECT) imaging device.

8. The nuclear imaging device of claim 1, further including:
   a subject support;
   a gantry which rotates around the subject support on an axis of rotation, the axis of rotation and the at least one radiation imaging device being disposed on the gantry with the slit parallel to the rotation axis.

9. The nuclear imaging device of claim 1, further including:
   a subject support;
   a gantry which rotates around the subject support on an axis of rotation, the axis of rotation and the at least one radiation imaging device being rotatably mounted to the gantry for rotation about an axis perpendicular to the two-dimensional detector array.

10. The nuclear imaging device of claim 1, further including:
    a subject support;
    a gantry which rotates around the subject support on an axis of rotation, the axis of rotation and the at least one radiation imaging device being disposed on the gantry and including a plurality of modules disposed in an array, each module including:
       a two-dimensional array of radiation detector elements which detect the emission radiation from the portion of the imaging region,
       a slit which focuses the emission radiation from the portion of the imaging region on the two-dimensional array of detector elements,
       a plurality of slats disposed perpendicular to the slit between the slit and the two-dimensional array of detector elements, the slats converging from the two-dimensional array of detector elements towards a focal line.

11. A SPECT imaging system comprising:
    at least one detector head which receives emission radiation from an imaging region, the detector head including an array of modules, each module detecting emission radiation from a portion of the imaging region and including:
       a two-dimensional array of radiation detector elements which detect the emission radiation from the portion of the imaging region,
       a slit which focuses the emission radiation from the portion of the imaging region on the two-dimensional array of detector elements,
       a plurality of slats disposed perpendicular to the slit between the slit and the two-dimensional array of detector elements, the slats converging from the two-dimensional array of detector elements towards a focal line,
    the modules being disposed adjacent each other in an array and the portions of the image region from which each module detects emission radiation being disposed adjacent each other.

12. The SPECT imaging device of claim 11, further including:
    a line source mounted to the gantry parallel to the axis of rotation.

13. The SPECT imaging system of claim 11, further including:
    a gantry which supports the at least one detector head for rotation on an axis of rotation around the imaging region.

14. The SPECT imaging system of claim 13, wherein at least one detector head is mounted on the gantry such that the slit aligns with the axis of rotation.

15. The SPECT imaging system of claim 11, wherein the modules are disposed in a two-dimensional array.

16. A nuclear imaging method comprising:
    emitting radiation from radioisotopes in an object in an imaging region;
    with a slit, projecting the emitted radiation onto a two-dimensional detector array;
    interposing a plurality of slats between the slit and the two-dimensional detector array, the slats being disposed perpendicular to the slit and converging away from the two-dimensional detector array;
    sampling the two-dimensional detector array to read out data indicative of a two-dimensional projection of the radiation emitted from the object.

17. The method of claim 16, further including:
    disposing the two-dimensional detector array, the slit, and the slats at each of a plurality of positions around the imaging region; and
    reconstructing projection data read out from the two-dimensional detector array at the plurality of positions into a three-dimensional image.

18. The method of claim 16, further including:
    rotating the two-dimensional detector array, the slit, and the slats, as a unit, around an axis perpendicular to the detector array.

19. The method of claim 16, further including:
    rotating the two-dimensional detector array, the slit, and the slats, as a unit, around the object in an axis of rotation;

disposing the slit parallel to the axis of rotation.

20. The method of claim 16, further including:

disposing a plurality of slits, two-dimensional detector arrays, and slats in an array with each slit projecting the emitted radiation from a different portion of the object on an associated one of the two-dimensional detector arrays.

* * * * *